United States Patent [19]

Walz et al.

[11] 4,385,000
[45] May 24, 1983

[54] SURFACE-ACTIVE PHOSPHONIC ACID ESTERS

[75] Inventors: Klaus Walz; Wilfried Nolte, both of Leverkusen; Friedhelm Müller, Odenthal, all of Fed. Rep. of Germany

[73] Assignee: Bayer Aktiengesellschaft, Leverkusen, Fed. Rep. of Germany

[21] Appl. No.: 131,525

[22] Filed: Mar. 18, 1980

[30] Foreign Application Priority Data

Mar. 24, 1979 [DE] Fed. Rep. of Germany ....... 2911696
Mar. 24, 1979 [DE] Fed. Rep. of Germany ....... 2911697

[51] Int. Cl.$^3$ .......................... B01J 13/00; C07F 9/40
[52] U.S. Cl. ..................................... 260/403; 252/311; 252/351; 252/356; 252/DIG. 17; 260/928; 260/929; 260/941; 260/943; 260/950; 260/952; 260/969
[58] Field of Search ............... 260/950, 403, 941, 943, 260/952

[56] References Cited

U.S. PATENT DOCUMENTS

| | | | |
|---|---|---|---|
| 2,587,340 | 2/1952 | Lewis et al. | 260/950 |
| 2,670,367 | 2/1954 | Lewis et al. | 260/950 |
| 2,677,700 | 5/1954 | Jackson et al. | 260/950 |
| 2,683,168 | 7/1954 | Jensen et al. | 260/950 |

OTHER PUBLICATIONS

Laughlin, "J. Org. Chem.," C, Vol. 27, (1962), 1005–1011.

*Primary Examiner*—Anton H. Sutto
*Attorney, Agent, or Firm*—Connolly and Hutz

[57] ABSTRACT

New surface-active phosphonic acid esters, which are inter alia suitable as emulsifiers and dispersants, a process for their preparation and emulsions and dispersions of water soluble polymers containing the new phosphonic acid esters and having high stability on storage.

2 Claims, No Drawings

SURFACE-ACTIVE PHOSPHONIC ACID ESTERS

The present invention relates to surface-active phosphonic acid esters, to a process for their preparation, to their use as emulsifiers and dispersants and to water-in-oil (W/O) emulsions and non-aqueous dispersions of water-soluble polymers containing these phosphonic acid esters. Accordingly, the present invention provides surface-active phosphonic acid esters corresponding to the following general formula (1)

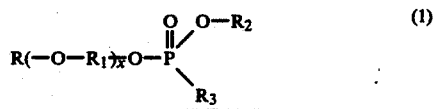

wherein R is an optionally substituted $C_8$–$C_{22}$ alkyl, alkenyl, acyl, aralkyl or alkaryl radical, $R_1$ is an ethylene and/or a 1,2-propylene radical, $R_2$ is a $C_1$–$C_4$ alkyl radical, a radical of the formula $R(-O-R_1)_x$ or a radical of the formula

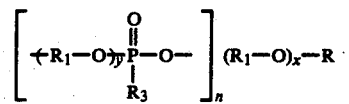

$R_3$ is a $C_1$–$C_8$ alkyl or alkenyl radical which may optionally be substituted or else optionally interrupted by ether oxygen atoms, and x is zero or an integer of from 1 to 100, y is an integer of from 1 to 20 and n is an integer of from 1 to 5.

Preferred radicals R are straight-chain alkyl or alkenyl radicals containing from 8 to 22 carbon atoms, such as the octyl, nonyl, dodecyl, tetradecyl, octadecyl, undecenyl and oleyl radicals, radicals of optionally unsaturated aliphatic or cycloaliphatic carboxylic acids containing from 8 to 22 carbon atoms such as, for example, lauric, stearic, oleic and abietic acid, and alkyl phenyl radicals containing from 8 to 22 carbon atoms, such as octyl phenyl, nonyl phenyl and dodecyl phenyl radicals. The radicals may each be optionally substituted once or several times, for example by halogen atoms, such as chlorine or bromine atom, or by cyano, carboxyl, $C_1$–$C_4$ alkoxy carbonyl, carbamoyl, hydroxy $C_1$–$C_4$ alkoxy groups.

With particular preference, R is a straight-chain, unsubstituted $C_8$–$C_{22}$ alkyl, alkenyl or acyl radical. In cases where the radicals $R_3$ are introduced into the phosphoric acid esters (1) by alkylation of the phosphorous acid esters (11) set out below, $R_3$ may be substituted in accordance with the alkylating agents described further below, for example by a halogen atom, a hydrocyl, carbamoyl, $C_1$–$C_4$ alkoxy carbonyl, $C_1$–$C_4$ halogen alkoxy or a 1,2-epoxy group or by a phenyl radical.

$R_3$ is preferably an optionally phenyl-substituted $C_1$–$C_4$ alkyl radical and, with particular preference, is a methyl, ethyl or benzyl radical.

The phosphonic acid esters according to the present invention of formula (1) above are produced either by reacting phosphorous acid esters corresponding to the following general formula (2)

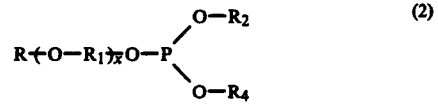

in which R, $R_1$, $R_2$ and x are as defined for formula (1) and $R_4$ is a $C_1$–$C_4$ alkyl radical, with alkylating agents by Arbuzov's method (Houben-Weyl, Methoden der organischen Chemie, Vol. X11/1, pages 500 et seq) or by rearranging these phosphorous acid esters, optionally in the presence of catalysts, such as methyl iodide, potassium iodide, triphenyl phosphine or toluene sulphonic acid methyl ester, to form the corresponding phosphonic acid esters.

Suitable alkylating agents are, preferably, aliphatic and araliphatic monofunctional and difunctional halogen compounds. Examples are alkyl halides, such as methyl iodide, ethyl chloride, bromide or iodide, propyl bromide, butyl iodide, allyl chloride, ethylene chloride, butylene chloride and dichlorohexane; derivatives of halogen carboxylic acids, such as chloroacetamide, chloropropionamide and chloroacetic acid methyl ester; halogen alcohols, such as chloroethanol, chloropropane diol and dichloropropanol; halogenated ethers and epoxides, such as epichlorhydrin, 2-methoxy ethyl chloride, 2-ethoxy ethyl chloride, dichlorodiethyl ether and 4,4'-dichlorodibutyl ether; and aralkyl halides, such as benzyl chloride. The monofunctional alkyl and aralkyl halides are particularly preferred.

The phosphorous acid esters corresponding to formula (2) which are used for producing the phosphonic acid esters corresponding to formula (1) may be obtained by known methods. For example, they may be produced by transesterifying phosphorous acid esters of lower alcohols with compounds corresponding to the formula (3)

optionally together with glycols corresponding to the formula

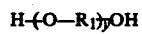

in which R, $R_1$, x and y are as defined for formula (1) above.

The reaction of the phosphorous acid esters of formula (2) with the alkylating agents may be carried out in known manner. The alkylating agents are advantageously added to the phosphorous acid esters in equimolar quantities at temperatures of from 50° to 200° C. and preferably at temperatures of from 100° to 160° C. Where halogen compounds are used as the alkylating agent, the lower alkyl halide formed is continuously distilled off from the reaction mixture. The alkylating agents may if desired, be used in excess particularly in the case of slow-reacting types.

In the case of simple rearrangements of the phosphorous acid esters corresponding to formula (2), in which the radical $R_4$ remains in the molecule, it is advantageous to heat a small portion of the ester, optionally together with a catalyst, to a temperature of from 120° to 200° C. and then to add slowly the rest of the ester at that temperature.

The phosphorous acid esters of formula (2) do not have to be used in a pure form for the reaction, and are preferably used in the form of mixtures of the type obtained during transesterification with lower trialkyl phosphites. Depending upon the molar ratio of component (3) to the lower trialkyl phosphite, the products obtained may contain the radical of component (3) once, twice and, in small amounts, even three times.

The phosphonic acid esters according to the present invention also include types containing two, three or more phosphonic acid ester groups in the molecule. These relatively high molecular weight phosphonic acid esters may be formed in addition to the monomolecular phosphonic acid esters during the rearrangement of phosphorous acid esters esterified with glycols corresponding to formula 4, or during the alkylation of the phosphorous acid esters with alkylating agents containing hydroxyl groups. For example, phosphonic acid esters corresponding to the following formula (5)

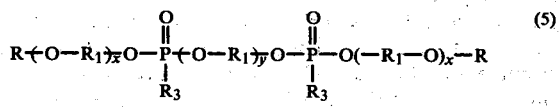

in which R, $R_1$, $R_3$, and x and y are as defined above, for formula (1), may be formed. These also have pronounced surface-active properties and, hence, may be used in the same way as the monomolecular phosphonic acid esters.

Preferred phosphonic acid esters correspond to the following formula (6)

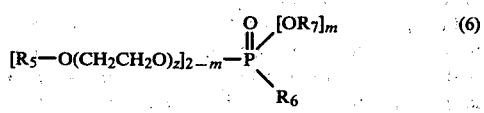

wherein
$R_5$ is an unsubstituted, straight-chain $C_8$–$C_{22}$ alkyl, alkenyl or acyl radical,
$R_6$ is a $C_1$–$C_4$ alkyl or alkenyl radical optionally substituted by an —OH, —$CONH_2$, —(COO)$C_1$–$C_4$-alkyl or phenyl radical, particularly the methyl, ethyl or benzyl radical,
$R_7$ is a methyl or ethyl radical,
z is an integer of from 2 to 30, preferably of from 6 to 12 and
m=0 or 1.

The above are produced either by reacting the transesterification products of 1 mole of an ethoxylation product of optionally unsaturated aliphatic $C_8$–$C_{22}$ alcohols or carboxylic acids and from 0.5 to 4 moles of trimethyl or triethyl phosphite with $C_1$–$C_4$ alkyl or alkenyl halides, chloroacetamide, chloroacetic acid esters, chloroethanol or benzyl chloride, or else by rearranging such transesterification products as the above, preferably thermally and optionally in the presence of catalysts, such as for example, methyl iodide, to form the corresponding phosphonic acid esters.

The compounds according to the present invention are surface-active and are suitable for numerous applications, such as, for example, washing agents, wetting agents, dyeing aids, emulsifiers and dispersants The compounds of the present invention are particularly suitable for use as wetting agents, dispersants and emulsifiers for oil dispersions of water soluble polymers. In this context, oils are generally understood to be hydrophobic organic liquids such as benzene, toluene, xylene, decalin, n- and i-paraffins, mineral oils, petroleum and mixtures thereof. Accordingly, the present invention also provides the use of phosphonic acid esters according to the present invention as wetting agents for rapidly dissolving water-soluble polymers present for example in the form of polymer/oil dispersions in water.

Non-aqueous dispersions of water-soluble polymers are known per se, and they are generally produced by polymerising water-soluble monomers in a W/O emulsion and subsequently removing the water, for example by azeotropic distillation, to a residual water content of less than 5% by weight. In addition to the emulsifiers used for polymerisation, dispersions such as these may contain suitable wetting agents to enable the polymers to be dissolved rapidly in water during their subsequent use. The production and use of polymer/oil dispersions such as these and also of the corresponding polymer-containing W/O emulsions are described for example in German Offenlegungsschriften Nos. 2,354,006 and 2,419,764. The dispersions in question are, in particular, dispersions of polyacrylamide and acrylamide copolymers in which the comonomer contains an ionic functional group, such as acrylic acid or dimethyl aminoethyl methacrylate. These polymers are primarily used as flocculating agents in the treatment of effluents, and also as retention agents in the paper industry.

For its application, the polymer/oil dispersion is stirred into water to form an aqueous solution of the polymer. In many cases, it is necessary to add wetting agents and emulsifiers which emulsify the oil in the water and enable the polymer to be dissolved rapidly. The emulsifiers used are, for example, ethoxylated nonyl phenols (German Offenlegungsschrift No. 2,419,764) or ethoxylated fatty alcohols (German Offenlegungsschrift No. 2,431,794).

In the preparation of the aqueous solution, the emulsifier and the polymer/oil dispersion are added to the water. However, it would be of greater advantage and also easier in terms of application to use only one product in which the emulsifier has been added to the dispersion during its production. In this case, however, unstable dispersions are generally obtained because the emulsifiers which are suitable for emulsifying oil in water are generally not sufficiently compatible with the oil. This applies in particular to paraffinic hydrocarbons.

It has been found that polymer dispersions and emulsions containing the new surface-active phosphonic acid esters have excellent stability and afford significant advantages with regard to the above-mentioned application.

Accordingly, the present invention also provides polymer/oil dispersions and water/oil emulsions of water-soluble polymers which comprise as emulsifier from 4 to 12% by weight, based on the weight of polymer, of a phosphonic acid ester corresponding to the following formula (1)

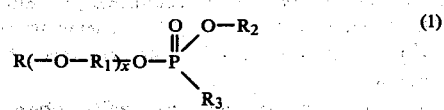

wherein
R is an optionally substituted $C_8$–$C_{22}$ alkyl, alkenyl, acyl, aralkyl or alkaryl radical,
$R_1$ is an ethylene and/or a 1,2-propylene radical,
$R_2$ is a $C_1$–$C_4$ alkyl, a radical of the formula R(O—$R_1$)$_x$ or a radical of the formula

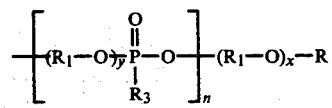

$R_3$ is a $C_1$–$C_8$ alkyl or alkenyl radical which may optionally be substituted or or else optionally interrupted by ether oxygen atoms, x is zero or an integer of from 1 to 100, y is an integer of from 1 to 20, and n is an integer of from 1 to 5.

Preferred radicals R are straight-chain alkyl or alkenyl radicals containing from 8 to 22 carbon atoms, such as the octyl, nonyl, dodecyl, tetradecyl, octadecyl, undecenyl or oleyl radical; radicals of optionally unsaturated aliphatic or cycloaliphatic carboxylic acids containing from 8 to 22 carbon atoms, such as lauric acid, stearic acid, oleic acid or abietic acid; and alkyl phenyl radicals containing from 8 to 22 carbon atoms, such as octyl phenyl, nonyl phenyl or dodecyl phenyl radicals. The radicals may each be substituted once or several times, for example by halogen atoms, such as chlorine or bromine, or by cyano, carboxyl, $C_1$–$C_4$ alkoxy carbonyl, carbamoyl, hydroxy or $C_1$–$C_4$ alkoxy groups. R is with particular preference a straight-chain, unsubstituted $C_8$–$C_{22}$ alkyl, alkenyl or acyl radical.

In cases where the phosphonic acid esters are produced by alkylating the corresponding phosphorous acid esters, $R_3$ may be substituted in accordance with the alkylating agents used, for example by a halogen atom, by a hydroxy, carbamoyl, $C_1$–$C_4$ alkoxy carbonyl, $C_1$–$C_4$ halogen alkoxy or 1,2-epoxy group or by a phenyl radical.

$R_3$ is preferably an optionally phenyl-substituted $C_1$–$C_4$ alkyl radical and, with particular preference, is a methyl, ethyl or benzyl radical.

The dispersions or emulsions of the present invention preferably contain phosphonic acid esters corresponding to the following formula (6)

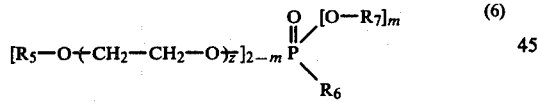

wherein $R_5$ is an unsubstituted straight-chain $C_8$–$C_{22}$ alkyl, alkenyl or acyl radical, $R_6$ is a $C_1$–$C_4$ alkyl or alkenyl radical optionally substituted by an —OH, —$CONH_2$, —(COO)$C_1$–$C_4$ alkyl or phenyl group, preferably by a methyl, ethyl or benzyl radical, $R_7$ is a methyl or ethyl radical, z is an integer of from 2 to 30, more preferably from 6 to 12, and m=0 or 1.

The present invention also relates to the use of the polymer emulsions and preferably the polymer dispersions containing the aforementioned phosphonic acid esters for the production of aqueous solutions of the polymers contained therein. For this purpose, the stable, storable dispersion of the polymer is, for example, mixed with water either directly or at a later stage, and this results in the formation of aqueous solutions of the polymer.

The water-soluble polymers present in the dispersions and emulsions according to the present invention may be produced by known methods, for example by thermal polymerisation in emulsion using radical initiators. They are, however, preferably produced in accordance with German Offenlegungsschrift No. 2,354,006 by the UV-polymerisation of water-soluble monomers in a W/O emulsion. Water-soluble monomers are understood to be monomers or salts thereof from which at least 2% by weight solutions can be prepared in water at 25° C.

The following are mentioned as examples of water-soluble compounds:

(A) water-soluble carboxylic acids containing from 3 to 6 and preferably 3 or 4 carbon atoms, such as acrylic acid, methacrylic acid, crotonic acid, maleic acid, itaconic acid, citraconic acid, aconitic acid and the alkali and ammonium salts thereof, preferably acrylic acid, methacrylic acid and maleic acid;

(B) water-soluble semiesters of di- and tri-carboxylic acids containing from 4 to 6 carbon atoms and monohydric aliphatic alcohols containing from 1 to 8 carbon atoms or the alkali and ammonium salts thereof, for example maleic acid semiester or its alkali and ammonium salts;

(C) α,β-mono-olefinically unsaturated sulphonic acids, such as vinyl sulphonic acid and styrene sulphonic acid;

(D) water-soluble, primary, secondary or tertiary aminoalkyl esters of (meth)acrylic acid containing from 2 to 4 carbon atoms in the alkyl moiety, such as for example dimethyl aminoethyl (meth)acrylate, diethylaminoethyl (meth)acrylate, dimethylaminopropyl (meth)acrylate and dimethylaminobutyl (meth)acrylate or salts thereof with inorganic or organic acids, such as hydrochloric acid and acetic acid, preferably dimethylaminoethyl (meth)acrylate;

(E) methacrylamide and acrylamide;

(F) dialkylamino alkyl (meth)acrylamides containing 1 or 2 carbon atoms in the alkylamino group and from 1 to 4 carbon atoms in the second alkyl group or salts thereof with inorganic or organic acids, such as hydrochloric acid and acetic acid, for example dimethylaminomethyl (meth)acrylamide; and (G) N-methylol (meth)acrylamide and N-alkoxymethyl (meth)acrylamides containing 1 or 2 carbon atoms in the alkoxy group, such as N-methoxymethyl (meth)acrylamide. It is preferred to use monomers of groups (A), (D), (E) and (F) or mixtures thereof.

One particularly preferred monomer mixture consists of from 90 to 60% by weight of acrylamide and from 10 to 40% by weight of dimethylaminoethyl methacrylate. The monomers are incorporated in statistical distribution in the same ratio in the copolymer.

The monomers or the salts thereof are used in the form of from 20 to 80% by weight and preferably form 50 to 70% by weight aqueous solutions for the polymerisation reaction.

The oil phase may be formed by any liquid which does not dissolve the monomers used and which is immiscible with water. It is preferred to use liquid aliphatic and aromatic hydrocarbons and their substitution products and mixtures, such as benzene, toluene, xylene, decalin, tetralin, mineral oils, kerosenes, petroleum, iso- and n-paraffins, petrol, white spirit, xylene mixtures or mixtures thereof.

The ratio by weight of the oil phase to the monomer-containing aqueous phase may be varied within wide limits according to which monomers are used but is preferably in the range from 3:1 to 1:2.5.

The polymer concentrations in the W/O emulsion may also vary within wide limits. The polymer content of the W/O emulsion accumulating normally amounts, however, to between 10 and 50% by weight.

The removal of water from the W/O emulsions to form the polymer/oil dispersion is normally performed by adding organic liquids which form azeotropic mixtures with water, such as benzene, toluene and heptane, followed by heating to boiling point. The organic liquid used as the oil phase is itself preferably used as the azeotropic dehydrating agent. The azeotropic mixture is distilled off, optionally under reduced pressure, and after condensation separates into an aqueous phase and an organic phase. This process is continued until almost all of the entire water has been removed from the polymer. The organic phase may if desired, be continuously returned to the reaction vessel through a water separator. Azeotropic distillation is generally carried out at temperatures below 100° C. and preferably at temperatures in the range of from 50° to 70° C., if desired, under reduced pressure.

The linear copolymers in the dispersions according to the present invention preferably have average molecular weights of at least 5,000,000.

To prepare the aqueous solutions of the polymers, the dispersions according to the present invention, which contain less that 5% by weight of water, based on the weight of polymer, may be mixed with water in situ, the dispersions preferably being introduced into water. The aqueous solutions preferably have a solids content of less than 5% by weight. Strictly speaking, the dispersions are converted into oil-in-water emulsions, although they have the visual appearance of clear solutions. In cases where they are to be used as retention agents and dehydration accelerators, the polymer solutions may have a solids contents of far less than 1% by weight.

The polymer concentration of the dispersions may vary within wide limits. The polymer content, however, normally amounts to between 10 and 50% by weight and preferably to between 30 and 50% by weight, based on the weight of polymer dispersion, and may be increased as required by distilling off further quantities of the oil phase.

The polymers remain in the dispersion in very finely divided form, preferably with a mean particle size of from 0.01 to 1μ, and are eminently suitable in this finely divided form for the production of aqueous polymer solutions which are preferably used as retention agents for fillers and as dehydration accelerators in the manufacture of paper. They may also be used as sizes for textiles, as finishing and thickening agents and as protective colloids.

The water/oil emulsions and polymer/oil dispersions according to the present invention which contain the new surface-active phosphonic acid esters may be produced by various processes known per se. For example, the emulsion polymerisation of the water-soluble monomers may be carried out using the phosphonic acid esters instead of known emulsifiers. In this way, it is possible to obtain emulsions directly and, after the azeotropic removal of water therefrom, dispersions according to the present invention. The dispersions may, of course, also be obtained by initially preparing a water-/oil emulsion using known emulsifiers, as described above, and then subsequently adding the phosphonic acid esters to the water/oil emulsion thus prepared either before or after removal of the water. Finally, the polymer/oil dispersion may be directly produced from the components described above by dispersing water-soluble polymers and phosphonic acid esters in oil.

The dispersions and emulsions according to the present invention have the following advantages.

The emulsifiers suitable for emulsifying oil in water are generally not sufficiently compatible with the oil, and this applies in particular to paraffinic hydrocarbons. In contrast, the new phosphonic acid esters are sufficiently compatible so that the quantities required may even be dispersed in dispersions based on paraffinic hydrocarbons without any of the separations which occur where emulsifiers of the ethoxylated fatty alcohol or nonyl phenyl type are used.

The new phosphonic acid ester emulsifiers are also superior to the known emulsifiers with regard to their effectiveness. Small quantities have the same emulsifying effect, particularly when the W/O emulsions used for producing the dispersion is co-ordinated with the new emulsifier.

Another advantage, particularly over ethoxylated nonyl phenols, lies in the relatively easy biodegradability of the phosphonic acid esters. In the treatment of effluents or in the paper industry, both the oil and also the emulsifier enter the effluent so that biodegradability is absolutely essential.

For this reason, unbranched aliphatic hydrocarbons are preferably used as the oils so that the advantage of the better compatibility of the phosphonic acid ester emulsifier and the higher stability and handling properties of the dispersions according to the present invention become particularly pronounced.

The present invention is further illustrated by the following Examples in which the parts and percentages quoted are always based on weight.

The production of the phosphonic acid esters is described in Examples 1 to 7. Example 8 demonstrates the better stability and effectiveness of the dispersions according to the present invention. For this purpose, a polymer/oil dispersion of cationic polyacrylamide is prepared, phosphonic acid ester and a conventional emulsifier are added and then water is stirred in after storage for 3 days.

The stability of the dispersion, the rate of dispersion in water (inversion) and the degree of dispersion in water after a few minutes are assessed.

The resulting solutions are added to a paper pulp of which the degree of fineness is subsequently determined by the Schopper-Riegler method.

EXAMPLE 1

48 parts of the phosphorous acid ester obtained as described below are heated with 5 parts of methyl iodide to a temperature of from 150° to 160° C. in a flask provided with a reflux condenser and a stirrer. Another 430 parts of the phosphorous acid ester are then added dropwise over a period of 1 hour at the same temperature. The reaction mixture is then stirred for 1 hour at 160°–170° C. and subsequently freed in vacuo from volatile constituents. 465 parts of a brown-yellow liquid are obtained, essentially consisting of the following phosphonic acid ester:

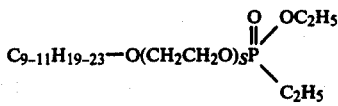

$n_D^{20} = 1.4637$, P-content: calculated 4.93%, observed 4.9%.

The phosphorous acid ester used above was obtained by transesterifying 266 parts of triethyl phosphite with 420 parts of a reaction product of 1 mole of a mixture of aliphatic C$_9$–C$_{11}$ alcohols with 8 moles of ethylene oxide at 160° C. The ethanol formed during the transesterification reaction was distilled off through a short column. Excess triethyl phosphite was distilled off in vacuo (up to 1 Torr) at 150° to 160° C.

EXAMPLE 2

30 parts of the phosphorous acid ester obtained as described below are mixed with 1.5 parts of methyl iodide, and the resulting mixture is heated to 140°–150° C. in a flask equipped with a reflux condenser and a stirrer. Another 430 parts of the phosphorous acid ester are then added dropwise over a period of 1 hour at the same temperature. The reaction mixture is then stirred for 5 hours at 150° C. The methyl iodide and any other volatile constituents are removed by the brief application of a vacuum. 450 parts of a phosphonic acid ester are obtained in the form of a red-brown, water-soluble liquid.

$n_D^{20} = 1.4604$, P-content: calculated, 2.8%, observed, 2.6%.

The phosphorous acid ester used above, which essentially has the following structure

was obtained by transesterifying 62 parts of trimethyl phosphite with 464 parts of an addition product of 6 moles of ethylene oxide with 1 mole of lauric acid at 120° to 140° C., 474 parts of the phosphorous acid ester being obtained.

EXAMPLE 3

86 parts of the phosphorous acid ester obtained as described below, which corresponds to the formula

are heated to 150°–160° C. with 5 parts of methyl iodide in a flask equipped with a reflux condenser and a stirrer, followed by the addition over a period of 1 hour of another 450 parts of the phosphorous acid ester. The reaction mixture is then stirred for 2 hours at 170° C., after which time volatile constituents are removed in vacuo. 555 parts of a phosphonic acid ester are obtained in the form of a water-soluble, low-viscosity liquid.

$n_D^{20} = 1.4650$, P-content: calculated 2.7%, observed 2.4%.

The phosphorous acid ester used above was obtained by reacting 83 parts of triethyl phosphite with 532 parts of an addition product of 6 moles of ethylene oxide with 1 mole of oleyl alcohol in the presence of 2 parts of diethyl phosphite at 160° to 180° C., the ethanol formed being continuously distilled off from the reaction mixture.

EXAMPLE 4

1.5 parts of methyl iodide are added to 39 parts of the phosphorous acid ester obtained as described below, and then is followed by heating the mixture to 150°–160° C. Another 360 parts of the phosphorous acid ester are then added dropwise over a period of from 1 to 2 hours at the same temperature. The reaction mixture is then stirred for 2 hours at 170° C. and subsequently freed from volatile constituents in vacuo at the same temperature. 395 parts of a brown, water soluble liquid are obtained. This solidifies to form a pale yellow crystalline mass which consists essentially of the following compound:

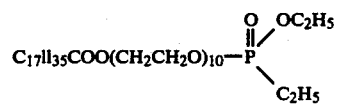

P-content: calculated 3.68%, observed 3.6%.
Turbidity point (1% aqueous solution): 58° C.

The phosphorous acid ester used above was obtained by reacting 166 parts of triethyl phosphite at 140°–150° C. with 362 parts of an addition product of 10 moles of ethylene oxide with 1 mole of stearic acid, the ethanol formed being continuously distilled off from the reaction mixture.

400 parts of the phosphorous acid ester were obtained.

EXAMPLE 5

3 parts of triphenyl phosphine are added to 296 parts of the phosphorous acid ester produced as described below, followed by heating to 160°–170° C. 50.6 parts of benzyl chloride are then added dropwise over a period of 40 minutes at the same temperature, the ethyl chloride formed being carried into a cold trap via a reflux condenser. The reaction mixture is then stirred for 5 hours at 170° to 190° C. and, after cooling to 150° C., the product is freed from volatile constituents under a vacuum of 1 Torr. 313 parts of a yellow liquid product corresponding essentially to the following formula

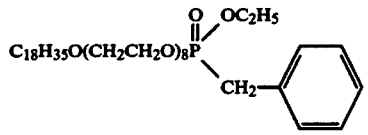

are obtained.

$n_D^{20} = 1.4815$, P-content: calculated 3.86%, observed 3.9%.

The phosphorous acid ester used above was produced by transesterifying 249 parts of triethyl phosphite with 465 parts of a reaction product of 1 mole of octadecenyl alcohol and 8 moles of ethylene oxide in the presence of 4 parts of diethyl phosphite at 160° to 170° C.

EXAMPLE 6

40 parts of the phosphorous acid ester produced as described below and 10 parts of toluene sulphonic acid methyl ester are heated to 180° C., followed by the addition over a prior of 1 hour of another 500 parts of the phosphorous acid ester. The reaction mixture is then stirred for 10 hours at 180° C. and is subsequently freed from volatile constituents under a vacuum of from 40 to 50 Torr. 530 parts of a yellow, water-soluble liquid consisting essentially of the following compound,

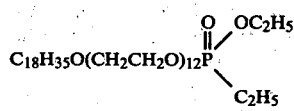

are obtained.

$n_D^{20} = 1.4639$, P-content: calculated 3.38%, observed 3.4%.

The phosphorous acid ester used above was produced by transesterifying triethyl phosphite with an addition product of 12 moles of ethylene oxide with 1 mole of oleyl alcohol. For this purpose, a mixture of 557 parts of the ethylene oxide adduct, 232 parts of triethyl phosphite and 3 parts of diethyl phosphite was heated to 145°–150° C. The ethanol formed was distilled off through a short column. Excess triethyl phosphite was distilled off at 145°–150° C. under a pressure of approximately 2 Torr. 611 parts of the phosphorous acid ester were obtained.

EXAMPLE 7

2 parts of methyl iodide are added to 70 parts of the phosphorous acid ester produced as described below, followed by heating to 160° C. Another 600 parts of the phosphorous acid ester are then added dropwise over a period of 30 minutes at the same temperature. The reaction mixture is kept at this temperature for 6 hours and is subsequently freed in vacuo from volatile constituents. 650 parts of a mixed phosphonic acid ester are obtained in the form of a water-soluble, light brown low-viscosity liquid.

$n_D^{20} = 1.4597$, P-content: 3.6%, OH-number: 35.

The phosphorous acid ester used above was produced by reacting 464 parts of an addition product of 6 moles of ethylene oxide with 1 mole of lauric acid, 185 parts of octaethylene glycol and 124 parts of trimethyl phosphite at 120° to 150° C., the methanol formed being distilled off through a column. 683 parts of a mixed phosphorous acid ester were obtained.

EXAMPLE 8

Two polymer/oil dispersions containing 30 parts of the sulphuric acid salt of a copolymer of 80% of acrylamide and 20% of dimethylaminoethyl methacrylate to 100 parts of a $C_{13}$–$C_{17}$ n-paraffin oil were tested. After their production, the dispersions still contain approximately 1 part of water and, based on copolymer, 3.6% of sorbitan monooleate and 3.9% of ethoxylated sorbitan hexa-oleate (dispersion 1) or 7.5% of sorbitan monooleate (dispersion 2).

Dispersions according to the present invention are produced therefrom by adding the phosphonic acid ester produced in accordance with Example 1 (wetting agent A). For comparison, dispersions are prepared with the conventional wetting agents NP10 and L7.

Wetting agent A:

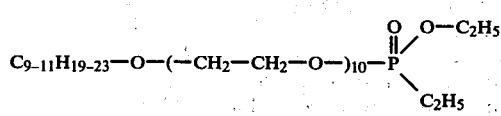

Wetting agent NP10:

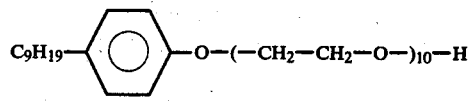

Wetting agent L7:

$C_{12}H_{25}$—O—$(CH_2$—$CH_2$—O—$)_7$—H

Assessment of the dispersions:

| Test No. | Wetting agent | Quantity | Dispersion | Stability of the dispersion | Inversion | Distribution |
|---|---|---|---|---|---|---|
| 1 | A | 6% | 1 | good | good | good |
| 2 | NP 10 | 6% | 1 | poor[1] | good | moderate |
| 3 | NP 10 | 10% | 1 | poor[2] | good | good |
| 4 | none | — | 1 | good | poor | poor |
| 5 | A | 10% | 2 | moderate[3] | good | good |
| 6 | NP 10 | 10% | 2 | poor[2] | good | good |
| 7 | L 7 | 10% | 2 | poor[2] | good | good |

[1]Emulsifier partly sediments;
[2]Emulsifier sediments; redispersible sediment of polymer;
[3]Small quanities of emulsifier sediment.

In cases where it is intended to use the dispersions containing added wetting agent, the stability of which was assessed as poor, thorough mechanical mixing has to carried out beforehand to homogenise the product.

The effectiveness of the products as flocculating agents or dehydration aids is primarily determined by the polymer. However, a basically good effectiveness level can be impaired by inadequate distribution, i.e. by inadequate emulsification of the oil phase in the water. Influence of the wetting agent on effectiveness:

| Test No. | Wetting agent | Quantity | Dispersion | Degree of fineness (SR) |
|---|---|---|---|---|
| 1 | A | 6% | 1 | 40 |
| 2 | NP 10 | 6% | 1 | 47 |
| 3 | NP 10 | 10% | 1 | 40 |
| comparison without flocculating agent | | | | 58 | comparison without flocculating agent

Equally good results are obtained with dispersions which contain phosphonic acid esters according to Examples 2 to 7 instead of the wetting agent A.

We claim:
1. Phosphonic acid esters of the formula

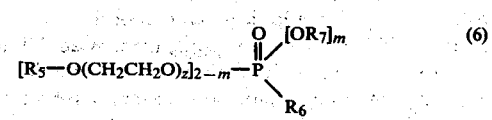

wherein $R_5$ is is an unsubstituted, straight-chain $C_8$–$C_{22}$ alkyl, alkenyl or acyl radical, $R_6$ is a $C_1$–$C_4$ alkyl or alkenyl radical optionally substituted by an —OH, —$CONH_2$, —$(COO)C_1$-$C_4$-alkyl or phenyl radical, $R_7$ is methyl or ethyl radical, z is an integer of from 2 to 30 and m=0 or 1.

2. Phosphonic esters as claimed in claim 1, characterised in that $R_6$ is a methyl, ethyl or benzyl radical and z is an integer of from 6 to 12.

* * * * *